United States Patent
Khvorova et al.

(10) Patent No.: US 9,334,495 B2
(45) Date of Patent: *May 10, 2016

(54) MINOR GROOVE BINDER (MGB)-OLIGONUCLEOTIDE MIRNA ANTAGONISTS

(75) Inventors: Anastasia Khvorova, Northborough, MA (US); Annaleen Vermeulen, Lafayette, CO (US); Rob Kaiser, Broomfield, CO (US); Jon Karpilow, Boulder, CO (US); Nicolaas M. J. Vermeulen, Woodinville, WA (US); Walt Mahoney, Woodinville, WA (US)

(73) Assignee: ELITECHGROUP B.V., Spankeren (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/953,098

(22) Filed: Nov. 23, 2010

(65) Prior Publication Data

US 2011/0172289 A1 Jul. 14, 2011

Related U.S. Application Data

(60) Provisional application No. 61/264,380, filed on Nov. 25, 2009.

(51) Int. Cl.
*C12N 15/11* (2006.01)
*C07H 21/02* (2006.01)
*C12Q 1/68* (2006.01)

(52) U.S. Cl.
CPC ........ *C12N 15/111* (2013.01); *C12N 2310/113* (2013.01); *C12N 2310/321* (2013.01); *C12N 2310/351* (2013.01)

(58) Field of Classification Search
CPC ................... C12Q 2525/207; C12Q 2600/178; C12N 15/113; C12N 2310/11; C12N 15/8218
See application file for complete search history.

(56) References Cited

U.S. PATENT DOCUMENTS

| | | | |
|---|---|---|---|
| 5,801,155 A | 9/1998 | Kutyavin et al. | |
| 6,312,894 B1 | 11/2001 | Hedgpeth et al. | |
| 7,045,610 B2 | 5/2006 | Dempcy et al. | |
| 7,381,818 B2 | 6/2008 | Lokhov et al. | |
| 7,575,863 B2 * | 8/2009 | Chen et al. | 435/6.12 |
| 7,582,739 B2 | 9/2009 | Lukhtanov et al. | |
| 8,163,708 B2 * | 4/2012 | Elmen et al. | 514/44 R |
| 2003/0175728 A1 * | 9/2003 | Belousov et al. | 435/6 |
| 2003/0181712 A1 * | 9/2003 | Nelson | 536/25.31 |
| 2005/0118623 A1 | 6/2005 | Belousov et al. | |
| 2006/0009628 A1 * | 1/2006 | Dempcy et al. | 536/23.1 |
| 2006/0229441 A1 | 10/2006 | Gall | |
| 2007/0123482 A1 * | 5/2007 | Stoffel et al. | 514/44 |
| 2009/0136957 A1 * | 5/2009 | Ivanovska et al. | 435/6 |

FOREIGN PATENT DOCUMENTS

| | | |
|---|---|---|
| WO | 2006/020768 | 2/2006 |
| WO | 2007/095387 | 8/2007 |
| WO | WO 2008/057234 | 5/2008 |
| WO | WO 2009/066967 | 5/2009 |

OTHER PUBLICATIONS

Maegdefessel et al., The Journal of Clinical Investigation, 2012, 122:497-506.*
Thomson et al., PLOS ONE, 2013, 8:e55214, pp. 1-7.*
Muller et al., Oncogene, 2008, 27:6698-6706.*
Gaur et al., Neuro-Oncology, 2011, 13:580-590.*
Swaminathan et al., PLOS Pathogens, 2012, 8:e1002937, pp. 1-23.*
Supratim Choudhuri, Lesser known relatives of miRNA, BBRC, 2009, vol. 388, pp. 177-180.*
European Patent Office, International Search Report and Written Opinion, Mar. 23, 2011.
Macron, Doug, Investment Firm Accelerator Launches miRNA Drug Developer, Licenses Nanogen MGB Tech, Aug. 21, 2008.
Anonymous, Nanogen Spins Out Firm and Plans to Merge with the Elitech Group, Aug. 15, 2008.
European Patent Office; Office Action; European Application No. 10788176.5; May 17, 2013; 4 pages.
Kumar, Surat, et al; Solution Structure of a Highly Stable DNA Duplex Conjugated to a Minor Groove Binder; Nucleic Acids Research, vol. 26, No. 3, 1998, pp. 831-838.
Kutyavin, Igor V., et al; Oligonucleotides With Conjugated Dihydropyrroloindole Tripeptides: Base Composition and Backbone Effects on Hybridization; Nucleic Acids Research, vol. 25, No. 18, 1997.
Chen, Jer-Kang, et al; Synthesis of Oligodeoxyribonucleotide N3'-P5' Phosphoramidates; Nucleic Acids Research, vol. 23, No. 14, 2661-2668, 1995.
Hutvagner, G., et al; Sequence-Specific Inhibition of Small RNA Function; PLoS Biology, 2(4), 0465-0475, Apr. 2004.
Kutyavin, I., et al; 3'-Minor Groove Binder-DNA Probes Increase Sequence Specificity at PCR Extension Temperatures; Nucleic Acids Research, vol. 28, No. 2, 655-661, 2000.
Meister, G., et al; Sequence-Specific Inhibition of MicroRNA- and SiRNA-Induced RNA Silencing; RNA, 10(3), 544-550, 2004.
Orom, U., et al; LNA-Modified Oligonucleotides Mediate Specific Inhibition of MicroRNA Function; Gene, 372, 137-141, 2006.
Vermeulen, A., et al; Double-Stranded Regions Are Essential Design Components of Potent Inhibitors of RISC Function, RNA, 13(5), 723-730, 2007.
European Patent Office; Response to Office Action; European Application No. 10788176.5; Sep. 18, 2013; 8 pages.
European Patent Office; Response to Office Action; European Application No. 10788176.5; Feb. 27, 2013; 13 pages.

(Continued)

*Primary Examiner* — Dana Shin
(74) *Attorney, Agent, or Firm* — Jackson Walker LLP

(57) ABSTRACT

Compositions and methods for inhibiting the actions of non-coding RNAs such as miRNAs and piRNAs are provided. The compositions comprise single or double stranded oligonucleotides conjugated with Minor Groove Binders ("MGBs"). The oligonucleotides can vary in length, can contain nucleotides having one or more modifications, and have regions that are substantially complementary to one or more mature miRNAs or piRNAs.

16 Claims, 6 Drawing Sheets

(56) References Cited

OTHER PUBLICATIONS

Chinese Patent Office; Office Action (in English); Chinese Application No. 201080059311.5; Oct. 12, 2013; 7 pages.
Macron, Doug; Investment Firm Accelerator Launches MiRNA Drug Developer, Licenses Nanogen MGB Tech; Genomeweb, Gene Silencing News; Aug. 21, 2008; 3 pages.
Chinese Patent Office; Response to Office Action in Chinese, Amended Claims in Chinese, Amended Claims in English; Chinese Application No. 201080059311.5; Feb. 27, 2014; 13 pages, Only the last page in English is considered.
Chinese Patent Office; Second Office Action in English, Chinese Application No. 201080059311.5; Jun. 27, 2014; 10 pages.
European Patent Office; Office Action; European Application No. 10788176.5; Jul. 28, 2014; 3 pages.

\* cited by examiner

MINOR GROOVE BINDER (MGB)-OLIGONUCLEOTIDE MIRNA ANTAGONISTS

This application claims priority to U.S. Provisional Patent Application Ser. No. 61/264,380, entitled "Minor Groove Binder (MGB)-Oligonucleotide miRNA Antagonists," filed on Nov. 25, 2009, the entire content of which is hereby incorporated by reference.

BACKGROUND

This invention relates to compositions and methods for inhibiting the actions of non-coding RNAs such as miRNAs and piRNAs.

RNA interference ("RNAi") is a near-ubiquitous pathway involved in post-transcriptional gene modulation. The key effector molecule of RNAi is the microRNA ("miRNA" or "miR"). These small, non-coding RNAs are transcribed as primary miRNAs ("pri-miRNA,"), shown in FIG. 1, and processed in the nucleus by Drosha (a Type III ribonuclease) to generate short hairpin structures called pre-miRNAs. These molecules are then transported to the cytoplasm and processed by a second nuclease (Dicer) to generate the mature, duplex form of the miRNA which is then capable of being incorporated in the RNA Induced Silencing Complex ("RISC"). Interactions between the mature miRNA-RISC complex and target messenger RNA ("mRNA") are (in part) mediated by the seed region of the miRNA guide strand (nucleotides 2-7) and lead to gene knockdown by transcript cleavage and/or translation attenuation.

Tools that enable researchers to understand the roles that miRNAs and miRNA targets play in disease, cellular differentiation, and homeostasis are invaluable. Such tools include but are not limited to miRNA inhibitors. Classes of miRNA inhibitors have been previously described (see Meister 2004 and Hutvagner 2004). These molecules are single stranded, range in size from 21-31 nucleotides ("nts") in length, and contain O-methyl substitutions at the 2' position of the ribose ring. Since the original discovery of miRNA inhibitors, multiple design elements have been identified and incorporated to enhance the efficacy of these molecules in a biological setting. For example, it has been demonstrated that inhibitors that have longer lengths or incorporate secondary structures (e.g. double stranded inhibitors) exhibit superior performance over the shorter 21-31 single stranded nucleotide design (Vermeulen et al. 2007). Other designs include the incorporation of locked nucleic acids ("LNAs") (Orom et al. 2006).

SUMMARY

The present invention provides compositions and methods for inhibiting the actions of non-coding RNAs such as miRNAs and piRNAs. The compositions comprise single or double stranded oligonucleotides conjugated with Minor Groove Binders ("MGBs"). The length of the oligonucleotide portion of the composition can vary considerably. Furthermore, the oligonucleotide can incorporate secondary structures including but not limited to those resulting from hairpins, bulges, and/or mismatches. Preferably the oligonucleotides contain a sequence that is (at least) substantially complementary (about 70%) to an endogenous mature miRNA or piRNA sequence or sequences.

Without wanting to be bound by theory, the improved performance of miRNA inhibitors likely results from increased binding affinity between the inhibitor and the target molecule. Thus, alternative strategies that enhance duplex stability or lock the inhibitor-miRNA-RISC complex in a more desirable conformation would further enhance the functionality of current miRNA inhibitor designs.

Oligonucleotides conjugated to Minor Groove Binders ("MGBs") can form stable duplexes with complementary sequences (Kutyavin, I. V., et al 2000). Though the mechanism behind MGB actions is yet to be fully understood, it has been suggested that MGBs induce conformational changes that enhance duplex stability. Similarly, conjugation of MGBs to short inhibitor molecules is expected to significantly enhance their potency over non-MGB inhibitors of similar size.

The minor groove binder component can also vary greatly and include any number of structures. Non-limiting examples of the MGB structures can be found in U.S. Pat. Nos. 5,801,155 and 7,582,739, incorporated herein by reference. These MGBs can be conjugated to the 5' and/or 3' terminus of one or more oligonucleotides, or can be associated with one or more nucleotides in the interior of an oligonucleotide.

The compositions disclosed herein are useful in various in vivo or in vitro methods for inhibiting miRNA actions. For example, the compositions can be used in treating a disease or condition characterized by over-expression of a miRNA by administering an optimal amount of an inventive MGB-antagonist against such miRNA.

DETAILED DESCRIPTION OF PREFERRED EMBODIMENTS

I. General

The present invention is directed to compositions and methods for inhibiting RNA interference, including siRNA, piRNA, and miRNA-induced gene silencing.

The present invention provides compositions and methods for inhibiting the actions of non-coding RNAs such as miRNAs and piRNAs. The compositions comprise single or double stranded oligonucleotides conjugated with Minor Groove Binders ("MGBs") through a linker. The oligonucleotide portion of the molecule can be composed of RNA, DNA, or RNA-DNA hybrids with any of the nucleotides of the above being modified or unmodified. The length of the oligonucleotide portion of the composition can vary considerably and range from as short as 6 nucleotides or base pairs (e.g., the minimal length of the seed region) to as long as 100 nucleotides or base pairs. Furthermore, the oligonucleotide can incorporate secondary structures including but not limited to those resulting from hairpins, bulges, and/or mismatches. Preferably the oligonucleotides contain a sequence that is (at least) substantially complementary (about 70%) to an endogenous mature miRNA or piRNA sequence or sequences.

Figure 1:
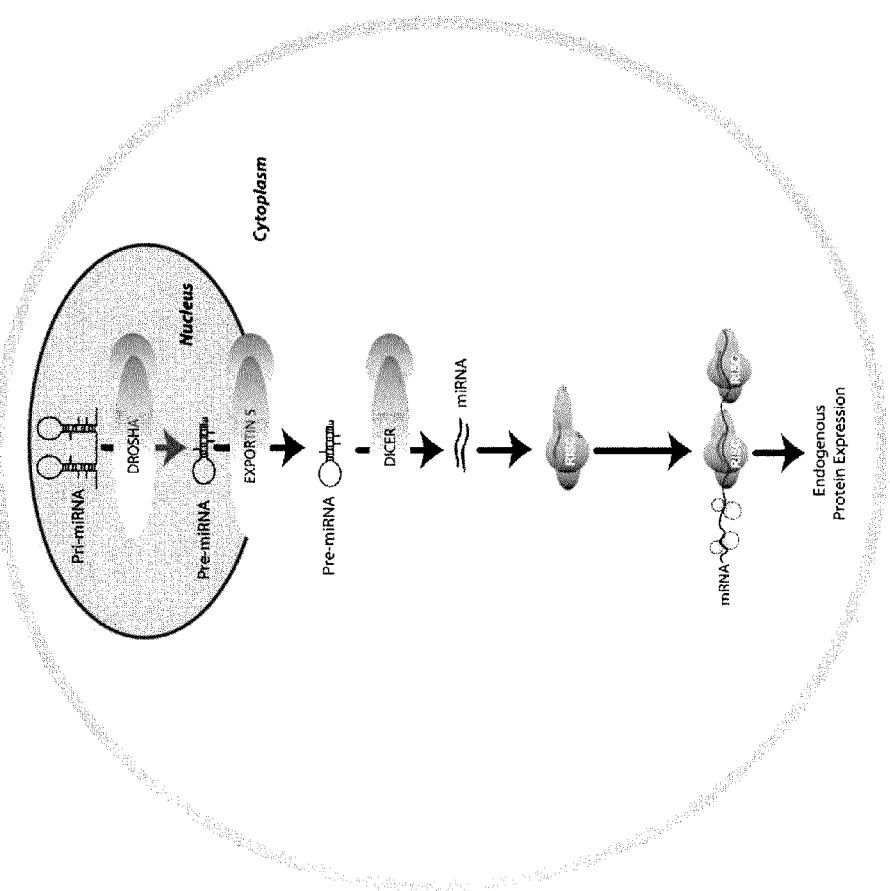
FIG. 1 shows a general schematic of the RNAi pathway.

FIG. 1 is a schematic describing the most basic details of the RNAi pathway. Endogenous miRNAs are first transcribed as pri-miRNAs that minimally consist of a hairpin structure with 5' and 3' flanking regions. Pri-miRNAs are processed by Drosha to yield pre-miRNAs that consist of simplified hairpin structures. Pre-miRNAs are transported out of the nucleus into the cytoplasm where they are further processed by Dicer into mature, duplex miRNAs capable of entering RISC and silencing gene expression by either mRNA cleavage or translation attenuation.

II. Definitions

Unless stated otherwise, the following terms and phrases have the meanings provided below:

The term "reporter" or "reporter gene" refers to a gene whose expression can be monitored. For example, expression levels of a reporter can be assessed to evaluate the success of gene silencing by substrates of the RNAi pathway.

The term "RNA Induced Silencing Complex," and its acronym "RISC," refers to the set of proteins that complex with single-stranded polynucleotides such as mature miRNA or siRNA, to target nucleic acid molecules (e.g., mRNA) for cleavage, translation attenuation, methylation, and/or other alterations. Known, non-limiting components of RISC include Dicer, R2D2 and the Argonaute family of proteins, as well as strands of siRNAs and miRNAs.

The term "RNA interference" and the term "RNAi" are synonymous and refer to the process by which a polynucleotide (a miRNA or siRNA) comprising at least one polyribonucleotide unit exerts an effect on a biological process. The process includes, but is not limited to, gene silencing by degrading mRNA, attenuating translation, interactions with tRNA, rRNA, hnRNA, cDNA and genomic DNA, as well as methylation of DNA with ancillary proteins.

The term "gene silencing" refers to a process by which the expression of a specific gene product is lessened or attenuated by RNA interference. The level of gene silencing (also sometimes referred to as the degree of "knockdown") can be measured by a variety of means, including, but not limited to, measurement of transcript levels by Northern Blot Analysis, B-DNA techniques, transcription-sensitive reporter constructs, expression profiling (e.g. DNA chips), qRT-PCR and related technologies. Alternatively, the level of silencing can be measured by assessing the level of the protein encoded by a specific gene. This can be accomplished by performing a number of studies including Western Analysis, measuring the levels of expression of a reporter protein that has e.g. fluorescent properties (e.g., GFP) or enzymatic activity (e.g. alkaline phosphatases), or several other procedures.

The terms "microRNA", "miRNA", or "miR" all refer to non-coding RNAs (and also, as the context will indicate, to DNA sequences that encode such RNAs) that are capable of entering the RNAi pathway and regulating gene expression. "Primary miRNA" or "pri-miRNA" represents the non-coding transcript prior to Drosha processing and includes the stem-loop structure(s) as well as flanking 5' and 3' sequences. "Precursor miRNAs" or "pre-miRNA" represents the non-coding transcript after Drosha processing of the pri-miRNA. The term "mature miRNA" can refer to the double stranded product resulting from Dicer processing of pre-miRNA or the single stranded product that is introduced into RISC following Dicer processing. In some cases, only a single strand of an miRNA enters the RNAi pathway. In other cases, two strands of a miRNA are capable of entering the RNAi pathway.

The term "mature strand" refers to the sequence in an endogenous miRNA that is the full or partial reverse complement of (i.e., is fully or partially complementary to) a target RNA of interest. The terms "mature sequence" or "targeting strand" and "targeting sequence" are synonymous with the term "mature strand" and are often used interchangeably herein.

The terms "MGB inhibitor," "MGB miRNA inhibitor," "MGB antagonist," and "MGB-oligonucleotide miRNA antagonist" are used interchangeably and refer to a molecule having an oligonucleotide component conjugated to a minor groove binder ("MGB") and capable of inhibiting the action of a miRNA or piRNA.

The term "target sequence" refers to a sequence in a target RNA, or DNA that is partially or fully complementary to the mature strand. The target sequence can be described using the four bases of DNA (A, T, G, and C), or the four bases of RNA (A, U, G, and C).

The term "target RNA" refers to a specific RNA that is targeted by the RNAi pathway, resulting in a decrease in the functional activity of the RNA. In some cases, the RNA target is an mRNA whose functional activity is its ability to be translated. In such cases, the RNAi pathway will decrease the functional activity of the mRNA by translational attenuation or by cleavage. In this disclosure, target RNAs are miRNAs, piRNAs, or related molecules whose function can be inhibited by binding. The term "target" can also refer to DNA.

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes, including the wobble base pair formed between U and G. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

The term "duplex" refers to a double stranded structure formed by two complementary or substantially complementary polynucleotides that form base pairs with one another, including Watson-Crick base pairs and U-G wobble pairs that allow for a stabilized double stranded structure between polynucleotide strands that are at least partially complementary. The strands of a duplex need not be perfectly complementary for a duplex to form, i.e., a duplex may include one or more base mismatches. In addition, duplexes can be formed between two complementary regions within a single strand (e.g., a hairpin).

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromouracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as in ethylphosphonates, phosphorothioates and peptides.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyl uridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoai nleotides, and alkylcarbonylalkylated nucleotides. Modified nucleotides also include those nucleotides that are modified with respect to the sugar moiety, such as by containing a 2'-O, 4'-C methylene bridge, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide is also meant to include what are known in the art as universal bases. By way of example, universal bases include, but are not limited to, 3-nitropyrrole, 5-nitroindole, or nebularine. The term "nucleotide" is also meant to include the N3' to P5' phosphoramidate, resulting from the substitution of a ribosyl 3'-oxygen with an amine group. Further, the term nucleotide also includes those species that have a detectable label, such as for example a radioactive or fluorescent moiety, or mass label attached to the nucleotide.

III. Description of the Embodiments

In one embodiment, a MGB miRNA inhibitor comprises an oligonucleotide component and an MGB-linker combination, with the linker having from about 3 to 100 main chain atoms, selected from C, O, N, S, P and Si. The linker can be a trivalent linker, a branched aliphatic chain, a heteroalkyl chain, one or more substituted ring structures, or combinations thereof. In one preferred embodiment, the inhibitor comprises a single stranded oligonucleotide that (1) can vary in length between 6-100 nucleotides in length, (2) has regions that are substantially complementary to one or more mature miRNAs or piRNAs or portions of mature miRNAs or piRNAs, and (3) is conjugated to one or more minor groove binders (MGB) through a linker. Preferably, the molecule comprises an MGB that is $DPI_3$ or $CDPI_3$.

Another embodiment pertains to a method for modulating gene expression; the method comprising introducing into a cell, in vitro or in vivo, an MGB miRNA inhibitor at a concentration such that the function of a target nucleic acid, preferably a miRNA or piRNA, is inhibited.

Another embodiment pertains to a method of treating a disease or condition that results from mis-expression of a gene or expression of a gene that has an undesirable function. The method comprises administering sufficient amounts of one or more MGB-miRNA inhibitors disclosed herein, with or without a suitable pharmaceutical carrier, to a patient suspected of having such a disease or condition.

Preferably one or more nucleotides of the oligonucleotide portion of the MGB inhibitor are modified. The preferred modification is an O-alkyl modification of the 2' carbon of the ribose ring of some or all of the nucleotides. Such modifications greatly enhance the affinity of the molecule for the target nucleic acid. That said, the MGB inhibitors of the invention exhibit multiple improvements over simple, modified single stranded inhibitors of equivalent length. Most importantly, MGB inhibitors exhibit enhanced potency of silencing.

Multiple design elements are taken into consideration when developing the highly functional MGB inhibitors described herein. These include (1) single stranded vs. multi-stranded designs, (2) oligonucleotide length, (3) oligonucleotide content (in the targeting portion and/or non-targeting portions of the oligonucleotide), (4) chemical modifications of the oligonucleotides, (5) the type of MGB conjugate, (6) the position of the MGB conjugate on the oligonucleotide, and (7) the type of linker that is used to associate the MGB moiety to the oligonucleotide. The following descriptions address each of these elements in greater detail.

A. Inhibitor Design

Inhibitor designs that are compatible with the MGB enhancements include both single stranded and multi-stranded designs. For example, the oligonucleotide portion of the inhibitor can be single stranded, fully double stranded, or a combination of single and double stranded regions (e.g., containing hairpin loop(s)). Additional details on MGB-compatible inhibitor designs can be found in WO2007/095387.

B. Oligonucleotide Length

The length of the oligonucleotide that is associated with an MGB can vary depending on a number of factors including the length of the endogenous miRNA being targeted by the molecule and the desired design attributes of the inhibitor. Mature miRNAs can vary in length from about 18 by to 28 base pairs. As such, in one embodiment, the length of the oligonucleotide conjugated to the MGB is the reverse complement to the mature strand of the miRNA being targeted. Reverse complements for all the known miRNAs can be determined from miRNA mature strand sequences which can be found in miRBase (microrna.sanger.ac.uk) which is maintained by the Sanger Institute. It should be noted that the list of sequences available in miRBase is predicted to increase as the number of miRNA sequences in all species expands. As such, the number of potential sequences that MGB-inhibitors can target is expected to grow.

In other instances, studies have shown that the performance of non-MGB inhibitors increases with increasing length (see Vermeulen et al 2007). As such, in another embodiment the MGB inhibitors can include sequences that flank the sequence which is the reverse complement of the miRNA being targeted. The length of these sequences vary greatly (5-100 nucleotides on the 5' and/or 3' end) and can comprise (1) the reverse complement of sequences flanking the mature sequence in the pre-miRNA or pri-miRNA, or (2) sequences partially related or unrelated to the reverse complement of the pre-miRNA or pri-miRNA.

C. The MGB Component of MGB miRNA Inhibitors

Multiple MGBs can be incorporated into the MGB-inhibitor design. In one non-limiting example, $DPI_3$ and $CDPI_3$ minor groove binder ligands can be attached to the oligonucleotide in any number of orientations using a wide range of linker chemistries known in the art. Preferably, the minor groove binders are conjugated to either the 3' or 5' end of the strand of the inhibitor that is the reverse complement to, e.g., the targeting strand of the target miRNA.

Figure 2A:
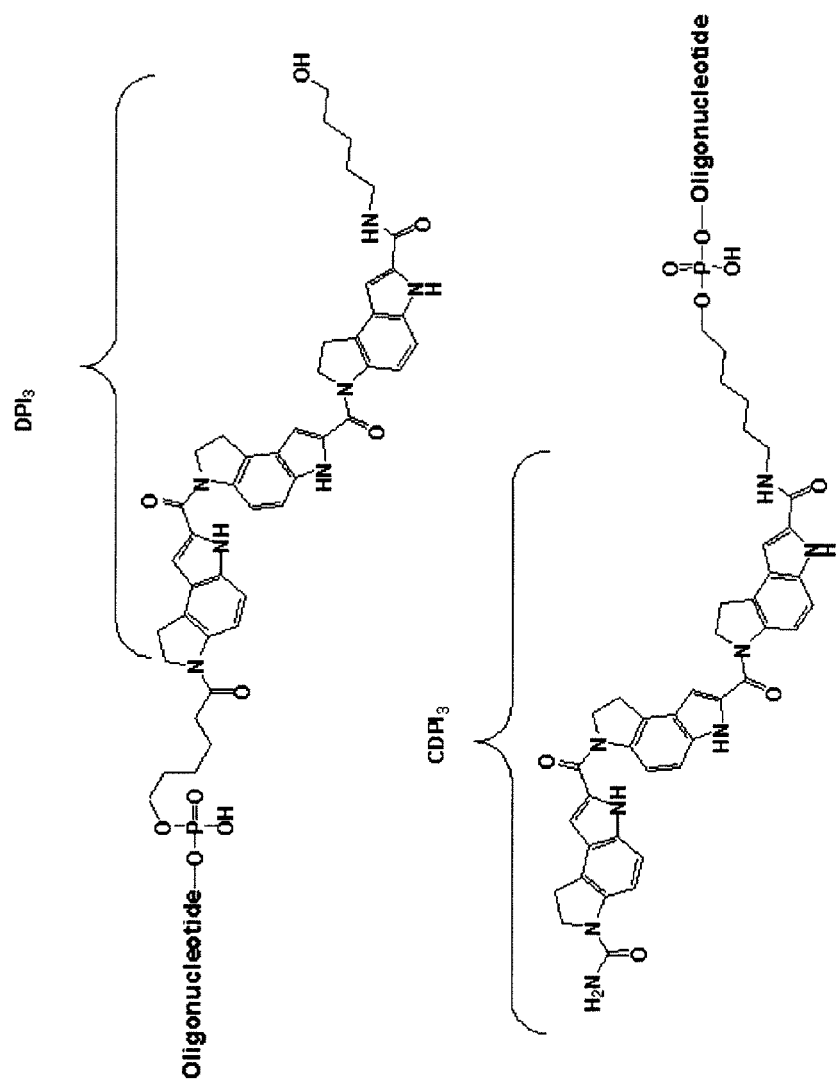
FIG. 2(a) shows a schematic of two MGB configurations (DPI$_3$ and CDPI$_3$ moieties) conjugated to oligonucleotides.
Figure 2B:
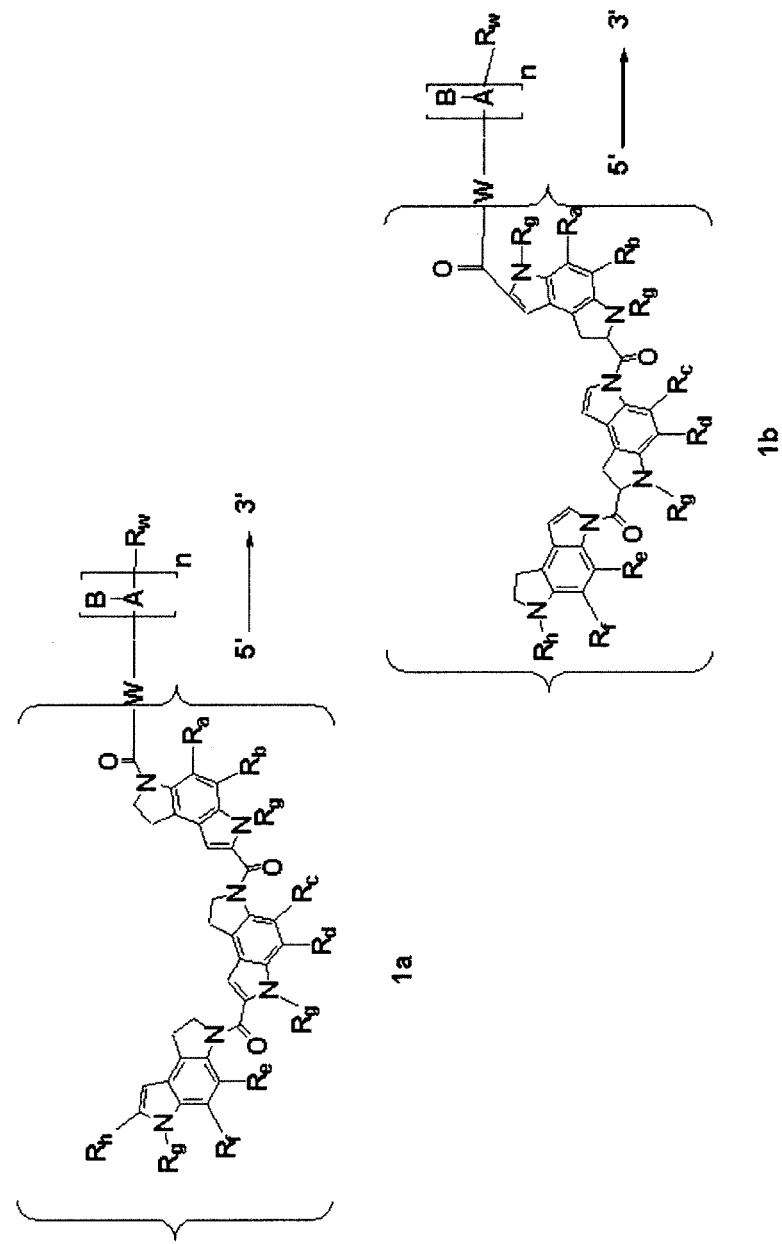
FIG. 2(b) shows a schematic of exemplary positions in which MGBs can be substituted.

FIG. 2(a) is a schematic of two MGB configurations ($DPI_3$ and $CDPI_3$ moieties) conjugated to oligonucleotides. FIG. 2(b) is a schematic showing positions in which MGBs can be substituted. In FIG. 2(b), W is a linker having from about 3 to 100 main chain atoms, selected from C, O, N, S, P and Si. Generally, W represents a trivalent linker, a branched aliphatic chain, a heteroalkyl chain, one or more substituted ring structures, or combinations thereof. $[A-B]_n$ represents a nucleic acid oligomer (e.g., DNA, RNA, PNA or any combination thereof; including those with modified bases and sugars) wherein A represents a sugar phosphate backbone, modified sugar phosphate backbone, locked nucleic acid backbone, peptidic backbone or a variant thereof used in nucleic acid preparation; and B represents a nucleic acid base, a modified base or a base analog as described in more detail below. The subscript n is an integer of from about 3 to about 100, preferably 6 to about 50 and more preferably 8 to about 20. The symbols $R_a$, $R_b$, $R_c$, $R_d$, $R_e$ and $R_f$ represent substituents selected from H, halogen, $(C_1-C_8)$alkyl, $OR_g$, $N(R_g)_2$, $N^+(R_g)_3$, $SR_g$, $COR_g$, $CO_2R_g$, $CON(R_g)_2$, $(CH_2)_mSO_3^-$, $(CH_2)_mCO_2^-$, $(CH_2)_mOPO_3^{-2}$, and $NHC(O)(CH_2)_mCO_2^-$, and esters and salts thereof, wherein each $R_g$ is independently H or $(C_1-C_8)$alkyl, and the subscript m is an integer of from 0 to 6. The symbol $R_h$ and $R_w$ represents H or a group (typically the vestige of a linking group used in solid phase synthesis) having from 1-30 atoms selected from C, N, O, P, and S which is either cyclic, acyclic, or a combination thereof; and having additional hydrogen atoms to fill the available valences. Additional examples of substituents can be found in U.S. Patent Application Publication No. 2005/0118623.

As stated above, the substituent A can include a deoxyribofuranose phosphate backbone or a ribofuranose phosphate backbone. In preferred embodiments the ribofuranose is substituted as shown below:

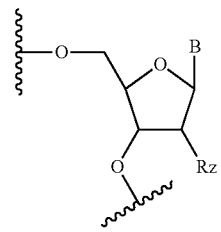

wherein Rz is $-OR^{aa}$ where $R^{aa}$ is $-O$-Alkyl$_{1-12}$, $-(CH_2)_n$O-Alkyl$_{1-12}$ where n is 1 to 6, halogen, or $-CF_3$; and B is a normal base or a modified base as defined above or in U.S. Pat. No. 7,045,610. The phosphate backbone of the modified oligonucleotides described above can also be modified so that the oligonucleotides contain phosphorothioate linkages and/or methylphosphonates and/or phosphoroamidates (Chen et al., Nucl. Acids Res., 23:2662-2668 (1995)). Combinations of oligonucleotide linkages in MB-oligonucleotide conjugates are also within the scope of the present invention. Still other backbone modifications are known to those of skill in the art.

Some minor groove binders contain different repeating units. Preferred minor groove binders are:

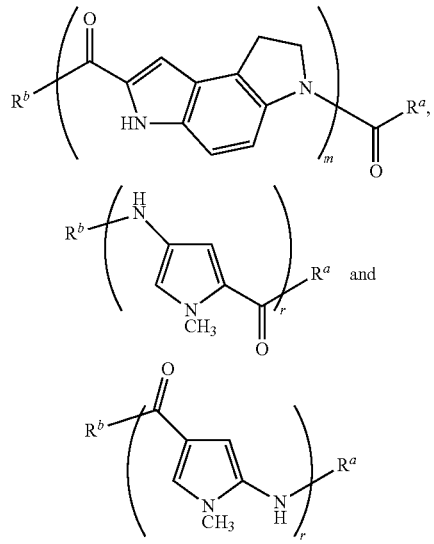

wherein the subscript m is an integer of from 2 to 5; the subscript r is an integer of from 2 to 10; and each $R^a$ and $R^b$ is independently a linking group to the oligonucleotide (either directly or indirectly through a quencher), H, $-OR^c$, $-NR^cR^d$, $-COOR^c$ or $-CONR^cR^d$, wherein each $R^c$ and $R^d$ is selected from H, $(C_2-C_{12})$heteroalkyl, $(C_3-C_{12})$heteroalkenyl, $(C_3-C_{12})$heteroalkynyl, $(C_1-C_{12})$alkyl, $(C_2-C_{12})$alkenyl, $(C_2-C_{12})$alkynyl, aryl$(C_1-C_{12})$alkyl and aryl, with the proviso that one of $R^a$ and $R^b$ represents a linking group to ODN or fluorophore. In an additional embodiment each of the rings in each structure can contain one or more additional substitutions selected from H, halogen, $(C_1-C_8)$alkyl, $OR_g$, $N(R_g)_2$, $N^+(R_g)_3$, $SR_g$, $COR_g$, $CO_2R_g$, $CON(R_g)_2$, $(CH_2)_mSO_3^-$, $(CH_2)_mCO_2^-$, $(CH_2)_mOPO_3^{-2}$, and $NHC(O)(CH_2)_mCO_2^-$, $AsO_{-3}^{2-}$, and esters and salts thereof, wherein each $R_g$ is independently H or $(C_1-C_8)$alkyl, and the subscript m is an integer of from 0 to 6. Additional details regarding these structures can be found in U.S. Patent Application Publication Nos. 2004/32665 and 2006/0229441.

Other Minor Groove Binders of interest have been disclosed in U.S. Pat. No. 6,312,894. In one group of embodiments, the MGB is selected from the group consisting of CC1065, lexitropsins, distamycin, netropsin, berenil, duocarmycin, pentamidine, 4,6-diamino-2-phenylindole, stilbamidine, 4,4'-diacetyldiphenylurea bis(guanylhydrazone) (DDUG), and pyrrolo[2,1-c][1,4]benzodiazepines or any of their analogs.

D. Oligonucleotide Content of an MGB Inhibitor

The oligonucleotide portion of the MGB inhibitors can consist of RNA, DNA, RNA-DNA hybrids and modifications of the same. In general, the sequence of some portion of each inhibitor is designed to be the reverse complement of a given miRNA expressed by the cell of interest. Alternatively, in cases where a miRNA is but one representative of a family of related sequences (e.g., let-7 family), the oligonucleotide portion of the MGB-inhibitor can comprise the reverse complement of, e.g., one family member, but have one or more bulges or base pair mismatches when aligned with other members in the miRNA family. As such, preferably the oligonucleotide portion of the MGB inhibitor is at least 70-80% complementarity to a target miRNA. More preferably the oligonucleotide portion of the MGB inhibitor has at least 80-99% complementarity to a target miRNA. And most preferably, the oligonucleotide portion of the MGB inhibitor has 100% complementarity to a target miRNA.

The nucleotides of the oligonucleotide portion of MGB inhibitors can contain a variety of chemical modifications that enhance the resilience against nuclease action, the deliverability of the molecule to cells, specificity, or the stability of the duplex (i.e. between the target miRNA and the oligonucleotide portion of the MGB inhibitor). Chemical modifications that provide these desired traits are well known in the art and include but are not limited to alterations/modifications of the base, the internucleotide linkage, as well as the sugar residue of the oligonucleotide. Some preferred modifications are listed below and are described in U.S. Pat. No. 7,045,610. These include 2'-O-alkyl modifications (e.g., 2'-O-methyl), 2' halogen modifications (e.g., 2' F), 5' and/or 3' cholesterol modifications and more. Furthermore, MGB inhibitors can include additional modifications that provide beneficial attributes to the molecule(s). Thus, for instance, MGB inhibitors can be further modified with, e.g., fluorescent dyes as well as, e.g., cholesterol modifications to enhance visualization and delivery of the MGB-inhibitors, respectively.

An example of a modification that can be associated with the polymeric backbone of the MGB antagonists is shown below:

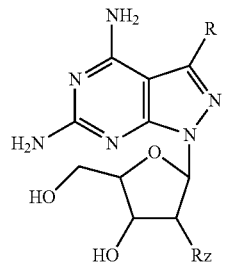

wherein Rz is —H and R=—C≡C—CH$_2$CH$_2$OH. This structure is also known as Super A.

E. Method of Introducing and Detecting the Effects of MGB-Inhibitors

The inhibitors of the present invention can be used in vitro, or administered to a cell or an animal including humans by any method known to one skilled in the art. For example, the molecules of the invention may be passively delivered to cells. Passive uptake of an inhibitor can be modulated, for example, by the presence of a conjugate such as a polyethylene glycol moiety or a cholesterol moiety, or any other hydrophobic moiety associated with the 5' terminus, the 3' terminus, or internal regions of the oligonucleotide. Alternatively, passive delivery can be modulated by conjugation of a ligand that is taken up by a cell through receptor mediated endocytosis. Other methods for inhibitor delivery include, but are not limited to, transfection techniques (using forward or reverse transfection techniques) employing DEAE-Dextran, calcium phosphate, cationic lipids/liposomes, microinjection, electroporation, immunoporation, and coupling of the inhibitors to specific conjugates or ligands such as antibodies, peptides, antigens, or receptors.

The method of assessing the level of inhibition is not limited. Thus, the effects of any inhibitor can be studied by one of any number of art tested procedures including but not limited to Northern analysis, RT PCR, expression profiling, and others. In one preferred method, a vector or plasmid encoding reporter whose protein product is easily assayed is modified to contain the target site (reverse complement of the mature miRNA, piRNA, or siRNA) in the 5'UTR, ORF, or 3'UTR of the sequence. Such reporter genes include alkaline phosphatase (AP), beta galactosidase (LacZ), chloramphenicol acetyltransferase (CAT), green fluorescent protein (GFP), variants of luciferase (Luc), and derivatives thereof. In the absence of the inhibitor, endogenous (or exogenously added) miRNAs target the reporter mRNA for silencing (either by transcript cleavage or translation attenuation) thus leading to an overall low level of reporter expression. In contrast, in the presence of the inhibitors of the invention, miRNA (piRNA, or siRNA) mediated targeting is suppressed, thus giving rise to a heightened level of reporter expression. Preferred reporter constructs include the psiCHECK-2 dual luciferase reporter (Promega).

IV. Applications

The inhibitors of the present invention may be used in a diverse set of applications, including basic research. For example, the present invention may be used to validate whether a miRNA or target of a miRNA is a target for drug discovery or development. Inventive inhibitors that inhibit a particular miRNA or a group of miRNAs are introduced into a cell or organism and said cell or organism is maintained under conditions that allow for specific inhibition of the targeted molecule. The extent of any decreased expression or activity of the target is then measured, along with the effect of such decreased expression or activity, and a determination is made that if expression or activity is decreased, then the target is an agent for drug discovery or development. In this manner, phenotypic effects can be associated with inhibition of particular target of interest, and in appropriate cases toxicity and pharmacokinetic studies can be undertaken and therapeutic preparations developed.

The molecules of the invention can be used to inhibit single or multiple targets simultaneously. Knockdown of multiple targets can take place by introducing pools of inhibitors targeting different molecules. Previous inhibitor designs lacked potency and as such, required high concentrations to partially inhibit e.g. a single miRNA. Introduction of pools of inhibitors using previous designs would require excessively high concentrations that can be cytotoxic. In contrast, the enhanced potency of the molecules of the invention enables users to inhibit one or more specific targets at concentrations that preserve the overall functionality of the RNAi pathway with minimal non-specific effects.

Because the inhibitors of the invention act independent of the cell type or species into which they are introduced, the present invention is applicable across a broad range of organisms, including but not limited plants, animals, protozoa, bacteria, viruses and fungi. The present invention is particularly advantageous for use in mammals such as cattle, horse, goats, pigs, sheep, canines, birds, rodents such as hamsters, mice, and rats, and primates such as, gorillas, chimpanzees, and humans.

The present invention may be used advantageously with diverse cell types, including but not limited to primary cells, germ cell lines and somatic cells. For example, the cell types may be embryonic cells, oocytes, sperm cells, adipocytes, fibroblasts, myocytes, cardiomyocytes, endothelium, neurons, glia, blood cells, megakaryocytes, lymphocytes, macrophages, neutrophils, eosinophils, basophils, mast cells, leukocytes, granulocytes, keratinocytes, chondrocytes, osteoblasts, osteoclasts, hepatocytes and cells of the endocrine or exocrine glands. Importantly, the present invention can be used to inhibit a broad range of miRNA, piRNA, and siRNAs including but not limited to (1) miRNA and piRNAs of the human genome implicated in diseases such as diabetes, Alzheimer's, and cancer, and (2) those associated with the genomes of pathogens (e.g. pathogenic viruses).

Still further, the present invention may be used in RNA interference applications, such as diagnostics, prophylactics, and therapeutics including use of the compositions in the manufacture of a medicament in animals, preferably mammals, more preferably humans in the treatment of diseases. In particular, the agents of the invention can be used to reverse the action of siRNAs, miRNAs, or piRNAs that are being used as therapeutic agents.

In the case of therapeutic or prophylactic purposes, dosages of medicaments manufactured in accordance with the present invention may vary from micrograms per kilogram to hundreds of milligrams per kilogram of a subject. As is known in the art, dosage will vary according to the mass of the mammal receiving the dose, the nature of the mammal receiving the dose, the severity of the disease or disorder, and the stability of the medicament in the serum of the subject, among other factors well known to persons of ordinary skill in the art. For these applications, an organism suspected of having a disease or disorder that is amenable to modulation by manipulation of a particular target nucleic acid of interest is treated by administering inhibitors of the invention. Results of the treatment may be ameliorative, palliative, prophylactic, and/or diagnostic of a particular disease or disorder.

Therapeutic or prophylactic applications of the present invention can be performed with a variety of therapeutic compositions and methods of administration. Pharmaceutically acceptable carriers and diluents are known to persons skilled in the art. Methods of administration to cells and organisms are also known to persons skilled in the art. Dosing regimens, for example, are known to depend on the severity and degree of responsiveness of the disease or disorder to be treated, with a course of treatment spanning from days to months, or until the desired effect on the disorder or disease state is achieved. Chronic administration of inhibitors of the invention may be required for lasting desired effects with some diseases or disorders. Suitable dosing regimens can be determined by, for example, administering varying amounts of one or more inhibitors in a pharmaceutically acceptable carrier or diluent, by a pharmaceutically acceptable delivery route, and amount of drug accumulated in the body of the recipient organism can be determined at various times following administration. Similarly, the desired effect can be measured at various times following administration of the inhibitor, and this data can be correlated with other pharmacokinetic data, such as body or organ accumulation. Those of ordinary skill can determine optimum dosages, dosing regimens, and the like. Those of ordinary skill may employ $EC_{50}$ data from in vivo and in vitro animal models as guides for human studies.

The inhibitors of the invention can be administered in a cream or ointment topically, an oral preparation such as a capsule or tablet or suspension or solution, and the like. The route of administration may be intravenous, intramuscular, dermal, subdermal, cutaneous, subcutaneous, intranasal, oral, rectal, by eye drops, by tissue implantation of a device that releases the inhibitor at an advantageous location, such as near an organ or tissue or cell type harboring a target nucleic acid of interest.

The foregoing embodiments are presented in order to aid in an understanding of the present invention and are not intended, and should not be construed, to limit the invention in any way. All alternatives, modifications and equivalents that may become apparent to those of ordinary skill upon reading this disclosure are included within the spirit and scope of the present invention.

EXAMPLES

The following examples are provided to illustrate, but not to limit, the presently claimed invention.

Example 1

Preparation of MGB Inhibitors $DPI_3$-modified oligonucleotides were prepared using $DPI_3$ solid DNA synthesis support as described in U.S. Pat. No. 7,381,818. The following steps were undertaken in the preparation of $CDPI_3$-modified oligonucleotides.

1. HPLC purification and salt exchange of amine-modified oligos. Amine-modified oligonucleotides (0.2-1 µmol synthesis scale) were dissolved in 0.1 M TEAB (triethylammonium bicarbonate) buffer to ~1 ml and chromatographed on a Luna C18 (10 µm) 4.6×250 mm column (Phenominex) eluting with a gradient of $CH_3CN$ in 0.1 M TEAB buffer. The product containing fraction were collected and dried in a SpeedVac concentrator until dry pellets were obtained.

2. $CDPI_3$ conjugation reaction. To each tube containing an amine-modified oligonucleotide (0.2-1 µmol initial DNA synthesis scale) was added a solution of 1 mg of $CDPI_3$ TFP ester shown below (and also further described in U.S. Pat. No. 5,801,155) and 2 ml TEA in 80 µl of DMSO. The tubes were gently swirled to dissolve the solids. The conjugation reactions were allowed to proceed for 5-18 hrs.

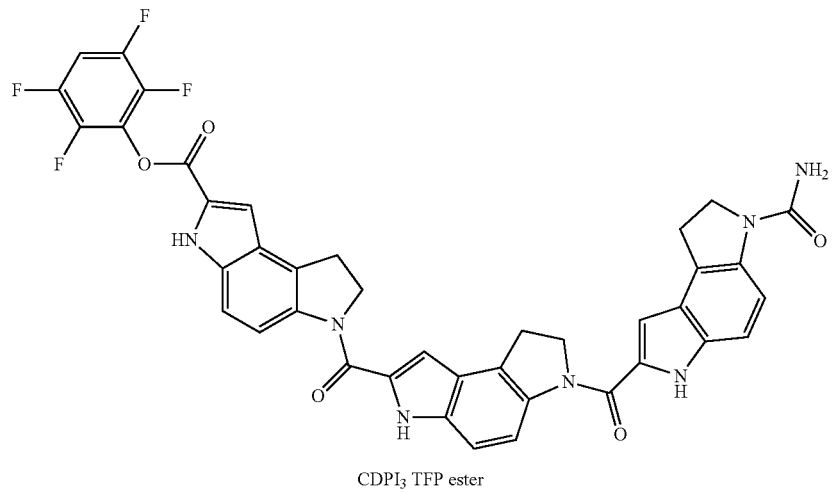 [SMILES: NC(=O)N1CCc2c1ccc1[nH]c(C(=O)N3CCc4c3ccc3[nH]c(C(=O)N5CCc6c5ccc5[nH]c(C(=O)Oc7c(F)c(F)cc(F)c7F)cc65)cc43)cc21]

$CDPI_3$ TFP ester

3. Conjugate purification. The reactions were diluted with 2 ml of 0.1 M TEAB buffer, loaded onto Luna C18 column and eluted with a gradient (8-40% of $CH_3CN$) in 0.1 M TEA B buffer. The product containing fraction were collected and dried in a SpeedVac concentrator until dry pellets were obtained.

Example 2

Assay for Assessing miRNA Inhibitor Function

Figure 3:
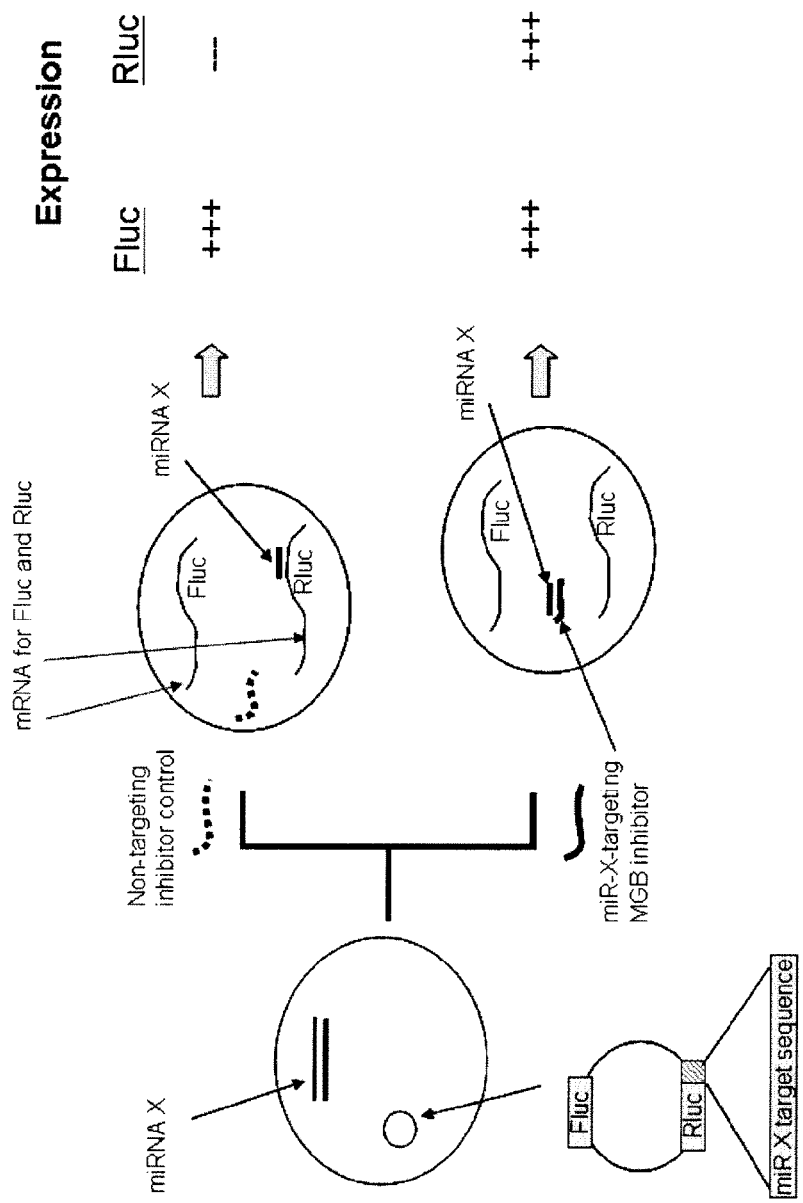
FIG. 3 shows a schematic of the dual luciferase assay.

For most of the experiments reported, quantitation of the level of inhibition was performed using the dual luciferase reporter system, psiCheck 2 (Promega). FIG. 3 is a schematic of the dual luciferase assay. The dual luciferase reporter contains both (1) the Fluc reporter and (2) an Rluc reporter containing a miRNA target site (miR-X target site) in the 3' UTR. In instances where (1) a non-targeting miRNA inhibitor control is present and (2) an endogenous miRNA (miRNA-X) capable of targeting the Rluc construct is expressed, the relative ratio of Rluc to Fluc is suppressed. In contrast, when a miRNA inhibitor capable of targeting the endogenously expressed miRNA (miRNA-X) is also present, the ability of the miRNA to target the Rluc construct is suppressed and therefore the Rluc to Fluc ratio is increased.

Briefly, the psiCheck plasmid encodes for two variants of luciferase, *Renilla* and Firefly. Target sequences were inserted into the multiple cloning site of the 3' UTR of the *Renilla* luciferase gene, thus allowing the Firefly sequence to be used as an internal control. To determine the practicality of different inhibitor designs, the oligonucleotide(s) of the invention and the modified psiCheck 2 plasmid were co-transfected into cells (100 ng of reporter DNA per well, 25-100 nM inhibitor, lipid=DharmaFECT Duo, Thermo Fisher Scientific). Twenty-four to ninety-six hours later cells were lysed and the relative amounts of each luciferase was determined using the Dual Glo Assay (Promega). For all experiments, unless otherwise specified, no significant levels of cellular toxicity were observed.

Firefly and *Renilla* luciferase activities were measured using the Dual-Glo™ Luciferase Assay System (Promega, Cat.# E2980) according to manufacturer's instructions with slight modification. When lysing cells, growth media was aspirated from the cells prior to adding 50 µL of firefly luciferase substrate and 50 µL *Renilla* luciferase substrate.

The Luciferase assays were all read with a Wallac Victor² 1420 multilabel counter (Perkin Elmer) using programs as recommended by the manufacturers.

Experimental design and data analysis: All treatments were run in triplicate. In addition, each experimental treatment with a reporter plasmid was duplicated with the psiCHECK™-2 control plasmid (no insert). To account for non-specific effects on reporter plasmids, experimental results are expressed as a normalized ratio $(Rluc/Fluc)_{norm}$: the ratio of *Renilla* luciferase expression to firefly luciferase expression for a given miRNA reporter plasmid $(Rluc/Fluc)_{miRNA}$ divided by the $(Rluc/Fluc)_{control}$ ratio for the identically treated psiCHECK™-2 reporter plasmid. The maximum values obtained from the reporter plasmid vary due to sequence. Ideally, values around 1 indicate low miRNA function, while values close to zero indicate high miRNA function. Data are reported as the average of the three wells and the error bars are the standard deviation of the three $(Rluc/Fluc)_{miRNA}$ ratios from the experimental treatment, scaled by the normalizing factor (the average of $(Rluc/Fluc)_{control}$). While ratios do not follow a normal distribution, the standard deviation values give a good sense of the variability of the data.

In cases where values between different miRNA reporter plasmids are compared, the maximum normalized $(Rluc/Fluc)_{norm}$ ratio was used as an additional scaling factor so that all reporters have a maximum of approximately 1. The additional scaling was performed for ease of comparison and does not affect the results.

Cell culture. HeLa cells were grown under standard conditions and released from the solid support by trypsinization. For most assays, cells were diluted to 1×10⁵ cells/ml, followed by the addition of 100 µL of cells/well. Plates were then incubated overnight at 37° C., 5% $CO_2$.

Example 3

Testing Different Designs of Minor Groove Binder Inhibitors

Using the Dual Luciferase Assay described above, a number of oligonucleotides, modified oligonucleotides and MGB-oligonucleotide conjugates were evaluated as inhibitors of miRNA function. The target sequences inserted into the 3' UTR of Rluc were Let7cTcomp from Table 1 (for Let7c) and _miR21Tcomp from Table 2 (for miR-21). The sequences for inhibitors of let-7c miRNA and miR-21 miRNA are shown in Table 1 and Table 2 respectively. In Tables 1 and 2, the presence of a 2'-O-Methylribofuranose sugar in an oligonucleotide is shown in bold italics. The presence of a Super A modified base is shown with a lower-case letter "a."

TABLE 1

Sequences of let7c and let7c inhibitors

| Inhibitor Abreviation | Sequence | Description |
|---|---|---|
| Let7c | 5'-UGAGGUAGUAGGUUGUAUGGUU-3' (Seq ID No: 1) | RNA mature strand |
| Let7cT | 5'-TGAGGTAGTAGGTTGTATGGTT-3' (Seq ID No: 2) | DNA equivalent mature strand |
| Let7cTcomp | 5'-AACCATACAACCTACTACCTCA-3' (Seq ID No: 3) | DNA complement |
| 2'Omet | 5'--*AACCATACAACCTAC TACCTCA*-3' (Seq ID No: 4) | Is a 2'-OMeRNA |
| DNA | 5'-AACCATACAACCTACTACCTCA-3' (Seq ID No: 3) | Is a DNA equivalent |

TABLE 1-continued

Sequences of let7c and let7c inhibitors

| Inhibitor Abreviation | Sequence | Description |
|---|---|---|
| 3MGB-DNA | 5'-AACCATACAACCTACTACCTCA-MGB-3' (Seq ID No: 5) | MGB is DPI$_3$ ligand |
| superA DNA | 5'-AaCCaTaCAaCCTaCTaCCTCA-3' (Seq ID No: 6) | "a" is Super A |
| 5MGB-DNA | 5'-MGB-AACCATACAACCTACTACCTCA-3' (Seq ID No: 7) | |
| SuperA 2'Omet | 5'-*A*a*CC*a*T*a*CA*a*CCT*a*CT*a*CCTCA*-3' (Seq ID No: 8) | "a" is Super A DNA; Other bases 2'-OMe |
| 5'MGB 2'Omet | 5'-MGB-*AACCATACAACCTACTACCTCA*-3' (Seq ID No: 9) | 5'-MGB-2'-OMe-RNA |
| 3'MGB-2'Omet | 5'-*AACCATACAACCTACTACCTCA*-MGB-3' (Seq ID No: 10) | 3'-MGB-2'-OMe-RNA |

TABLE 2

Sequences of mir21 and mir 21 inhibitors

| Inhibitor Abreviation | Sequence | Description |
|---|---|---|
| mir21 | 5'-UAGCUUAUCAGACUGAUGUUGA-3' (Seq ID No: 11) | RNA mature strand |
| mir21T | 5'-TAGCTTATCAGACTGATGTTGA-3' (Seq ID No: 12) | DNA equivalent mature strand |
| mir21Tcomp | 5'-TCAACATCAGTCTGATAAGCTA-3' (Seq ID No: 13) | DNA complement |
| 2'Omet | 5'-*TCAACATCAGTCTGATAAGCTA*-3' (Seq ID No: 14) | Is a 2'-OMeRNA |
| DNA | 5'-TCAACATCAGTCTGATAAGCTA-3' (Seq ID No: 13) | Is a DNA equivalent |
| 3MGB-DNA | 5'-TCAACATCAGTCTGATAAGCTA-MGB-3' (Seq ID No: 15) | MGB is DPI$_3$ ligand |
| superA DNA | 5'-TCaaCaTCaGTCTGaTAaGCTA-3' (Seq ID No: 16) | "a" is Super A is a 2'-deoxyribonucleotide |
| 5MGB-DNA | 5'-MGB-TCAACATCAGTCTGATAAGCTA-3' (Seq ID No: 17) | MGB is DPI$_3$ ligand |
| SuperA 2'Omet | 5'--TCaa*C*aTC*a*GTCTG*a*TA*a*GCTA-3' (Seq ID No: 18) | "a" is Super A DNA; Other bases 2'-OMe |
| 5'MGB 2'Omet | 5'MGB-*TCAACATCAGTCTGATAAGCTA*-3' (Seq ID No: 19) | 5'-MGB-2'-OMe-RNA |
| 3'MGB-2'Omet | 5'-*TCAACATCAGTCTGATAAGCTA*-3' (Seq ID No: 20) | 3'-MGB-2'-OMe-RNA |

FIG. 4 shows the performance of the multiple miRNA inhibitor designs. Inhibitors of different designs were introduced into cells together with the appropriate (let-7c or miR-21) dual luciferase reporter construct. Controls consisted of untreated cells (none) or cells treated with simple, 2'-O methyl modified reverse complement inhibitor molecules (2'-Omet).

Figure 4A:
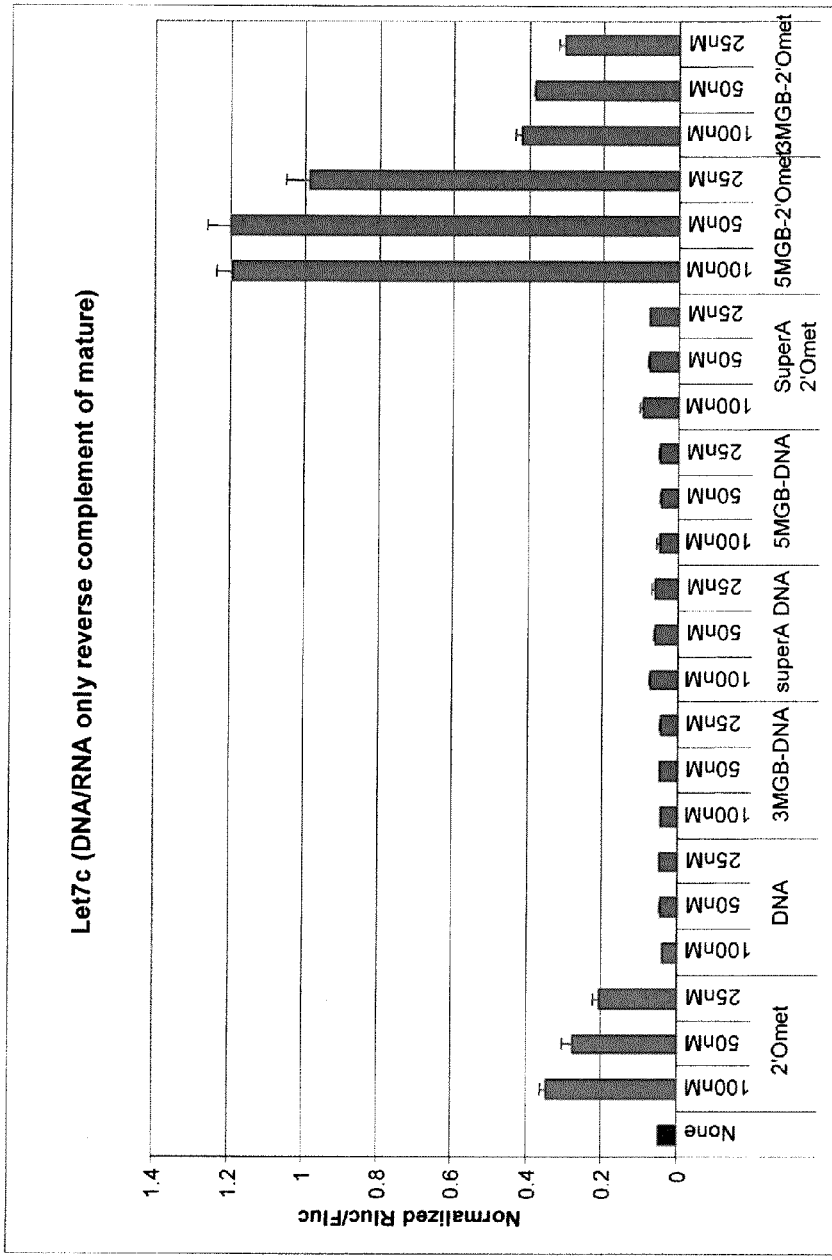
FIG. 4a shows the performance of multiple miRNA inhibitor designs on the let-7c dual luciferase reporter construct.
Figure 4B:
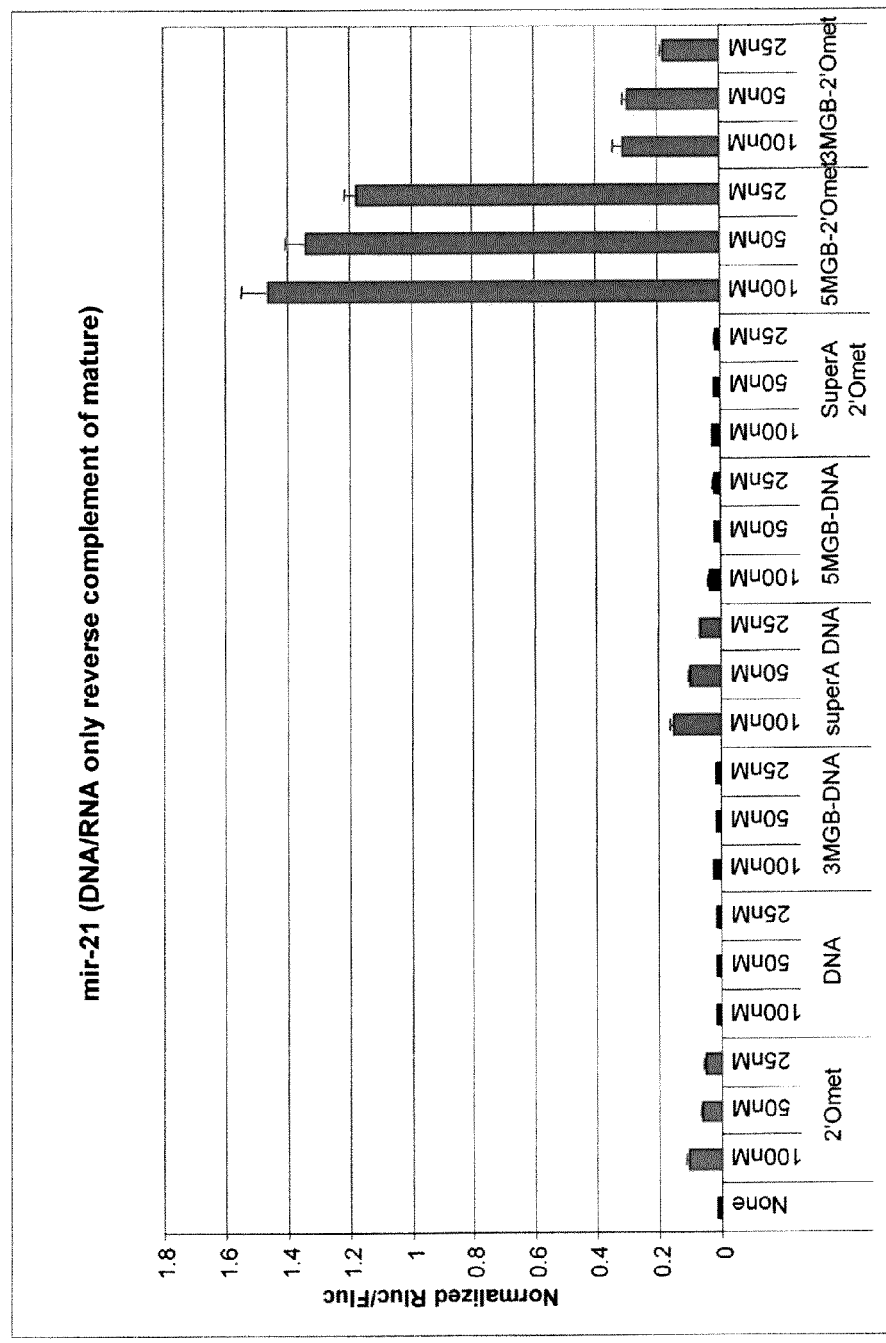
FIG. 4b shows the performance of multiple miRNA inhibitor designs on the miR-21 dual luciferase reporter construct.

The performance of let-7c inhibitors is shown in FIG. 4a. A baseline ratio of Rluc/Fluc was obtained in the absence of any inhibitor molecule (see "none"). Compared to the untreated control (none) 2'-O methyl modified single stranded inhibitors (2'Omet) showed an increase in the Rluc/Fluc ratio, indicating that this design is capable of providing some level of let-7c inhibition. The "DNA", "3'-MGB-DNA", "5'-MGB-DNA", "Super A substituted DNA" (which refers to a 2'-deoxyribonucleoside disclosed in U.S. Pat. No. 7,045,610) and the chimera-"Super A-2'Omet" showed baseline levels of inhibition similar to the untreated controls, suggesting that these design configurations were incapable of inhibiting let-7c function. However, while the "3'-MGB-2'-OMet" induced similar levels of inhibition as 2'-Omet, the 22-mer "5'-MGB-2'-OMe" induced roughly 3.4 fold greater levels of inhibition as the 2'-Omet design. Results from a parallel experiment performed on miR-21 show very similar results (see FIG. 4b). The 5'-MGB-2'-OMet and 3'-MGB-2'-OMet inhibitor configurations exhibited roughly 10× and 3× performance improvements over the 2'-Omet design, respectively.

REFERENCES

U.S. Patent Documents

U.S. Pat. No. 5,801,155
U.S. Pat. No. 6,312,894
U.S. Pat. No. 7,045,610
U.S. Pat. No. 7,381,818
U.S. Pat. No. 7,582,739
U.S. Patent Application Publication No. 2004/32665
U.S. Patent Application Publication No. 2005/0118623
U.S. Patent Application Publication No. 2006/0229441

International Patent Documents

PCT Application Publication No. WO2007/095387

Other Publications

Chen et al., Nucl. Acids Res., 23:2662-2668 (1995)
Hutvagner, G. et al. (2004) "Sequence-specific inhibition of small RNA function." PLoS Biol. April; 2(4):E98
Kutyavin, I. V., et al, (2000) "3'-Minor groove binder-DNA probes increase sequence specificity at PCR extension temperatures." NAR, 28(2):655-661
Meister, G. et al, (2004) "Sequence-specific inhibition of microRNA- and siRNA-induced RNA silencing." RNA 10(3):544-50
Orom et al, (2006) "LNA-modified oligonucleotides mediate specific inhibition of microRNA function" Gene 372:137-141
Vermeulen et al. RNA, 2007 13(5):723-30

What is claimed is:

1. An inhibitor composition for inhibiting non-coding RNAs comprising:
an oligonucleotide; and
a minor groove binder (MGB), wherein the oligonucleotide comprises nucleotides, wherein all nucleotides of the oligonucleotide comprise ribofuranose having the following structure:

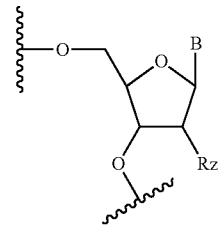

wherein Rz is —OCH$_3$, and wherein B is a normal base or a modified base, wherein the nucleotides are linked by natural phosphodiester linkages, and wherein the MGB is conjugated to the 5' end of the oligonucleotide.

2. The inhibitor composition of claim 1 further comprising a linker through which the MGB is attached to the oligonucleotide.

3. The inhibitor composition of claim 2 wherein the linker comprises from about 3 to about 100 atoms in a chain selected from the group consisting of C, O. N, S, P. and Si.

4. The inhibitor composition of claim 2 wherein the linker comprises a trivalent structure, a branched aliphatic chain, a heteroalkyl chain, one or more substituted ring structures, or a combination thereof.

5. The inhibitor composition of claim 1 wherein the oligonucleotide comprises one or more modified bases.

6. The inhibitor composition of claim 5 wherein the one or more modified bases comprise 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine, 5-(2-amino)propyl uridine, 5-halocytidine, 5-halouridine, 4-acetyleytidine, 1-methyladenosine, 2-methyladenosine, 3-methylcytidine 6-methyluridine, 2-methylguanosine, 7-methylguanosine, 2,2-dimethylguanosine, 5-methylaminoethyluridine, 5-methyloxyuridine, 7-deaza-adenosine, 6-uzeuridine, 6-azocytidine, 6-azothymidine, 5-methyl-2-thiouridine, 2-thiouridine, 4-thiouridine, 2-thiocytidine, dihydrouridine, pseudouridine, queuosine, archaeosine, naphthyl groups, N6-methyladenosine, 5-methylcarbonylmethyluridine, uridine 5-oxyacetic acid, pyridine-4-one, pyridine-2-one, aminophenol, 2,4,6-trimethoxy benzene, 8-substituted adenines and guanines, azapyrimidines, carboxyhydroxyalkyl nucleotides, carboxyalkylaminoai nucleotides, alkylcarbony lalkylated nucleotides, and combinations thereof.

7. The inhibitor composition of claim 5, wherein the one or more modified bases comprise one or more bases having 2' halogen modifications.

8. The inhibitor composition of claim 1, wherein the oligonucleotide comprises one or more universal bases.

9. The inhibitor composition of claim 1, wherein the oligonucleotide comprises one or more nucleotides having a detectable label.

10. The inhibitor composition of claim 1, wherein the oligonucleotide comprises a sequence that is a complement to a mature strand of a target sequence.

11. The inhibitor composition of claim 1, wherein the MGB is DPI$_3$ or CDPI$_3$.

12. The inhibitor composition of claim 1, wherein the MGB comprises a structure selected from the following group:

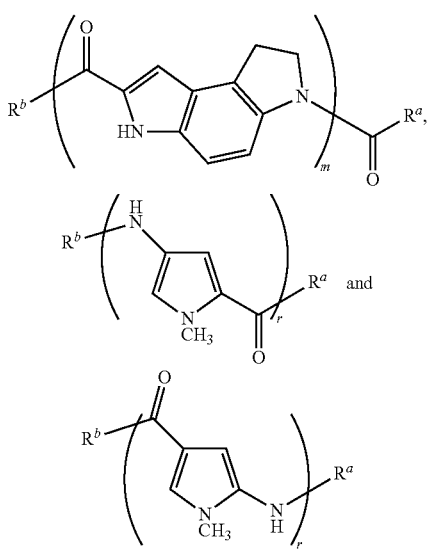

wherein the subscript m is an integer of from 2 to 5;
the subscript r is an integer of from 2 to 10; and
each $R^a$ and $R^b$ is independently a linker to the oligonucleotide, a linker to a fluorophore, H, —$OR^c$, —$NR^cR^d$, —$COOR^c$ or —$CONR^cR^d$, wherein each $R^c$ and $R^d$ is selected from H, ($C_2$-$C_{12}$)heteroalkyl ($C_3$-$C_{12}$)heteroalkenyl, ($C_3$-$C_{12}$)heteroalkynyl, ($C_1$-$C_{12}$)alkyl, ($C_2$-$C^{12}$)alkenyl, ($C_2$-$C_{12}$)alkynyl, aryl($C_1$-$C_{12}$)alkyl and aryl, wherein one of $R^a$ and $R^b$ is a linker to the oligonucleotide or to a fluorophore.

13. The inhibitor composition of claim 12 wherein the rings in the structures contain one or more substitutions selected from H, halogen, ($C_1$-$C_8$)alkyl, $OR_g$, $N(R_g)_2$, $N^+(R_g)_3$, $SR_g$, $COR_g$, $CO_2R_g$, $CON(R_g)_2$, $(CH_2)_mSO_3^-$, $(CH_2)$, $CO_2^-$, $(CH_2)_mOPO_3^{-2}$, and $NHC(O)(CH_2)_mCO_2^-$ and esters and salts thereof, wherein each $R_g$ is independently H or ($C_1$-$C_8$)alkyl, and the subscript m is an integer of from 0 to 6.

14. The inhibitor composition of claim 1 wherein the inhibitor composition comprises one of the following structures:

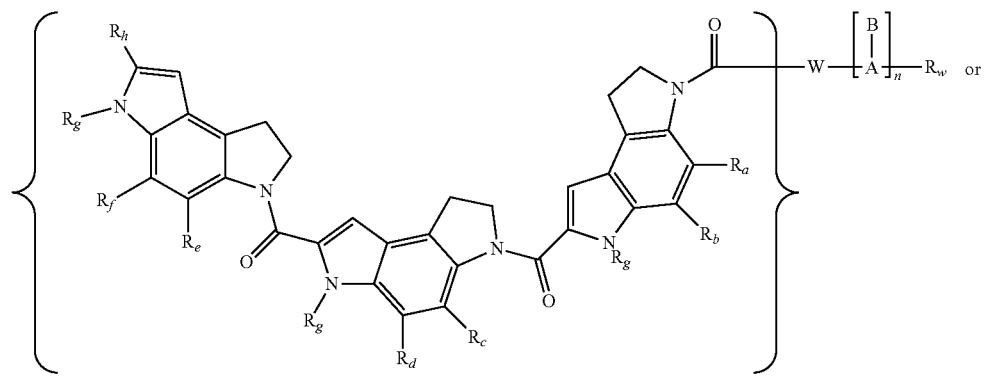

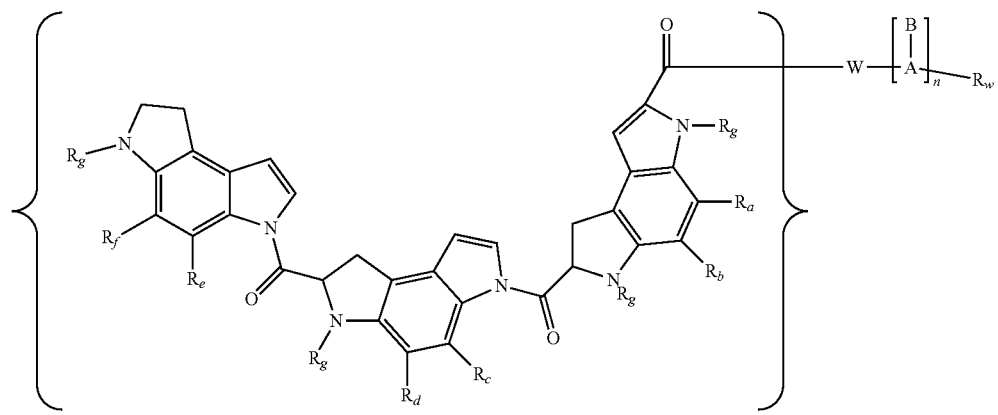

wherein W is a linker having from about 3 to 100 main chain atoms, selected from C, O, N, S, P and Si;

[A-B]$_n$ is an oligonucleotide wherein A represents a sugar phosphate backbone, modified sugar phosphate backbone, locked nucleic acid backbone, peptidic backbone or a variant thereof used in nucleic acid preparation, wherein W is connected to the 5' end of [A-B]$_n$, and wherein [A-B]$_n$ comprises nucleotides comprising ribofuranose having the following structure:

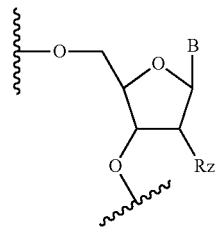

wherein Rz is —OCH$_3$, and B is a base, and wherein the nucleotides are linked by natural phosphodiester linkages;

n is an integer of from about 3 to about 100;

$R_a$, $R_b$, $R_c$, $R_d$, $R_e$ and $R_f$ are substituents selected from H, halogen, (C$_1$-C$_8$)alkyl, OR$_g$, N(R$_g$)$_2$, N$^+$(R$_g$)$_3$, SR$_g$, COR$_g$, CO$_2$R$_g$ CON(R$_g$)$_2$(CH$_2$)$_m$SO$_3^-$, (CH$_2$)$_m$CO$_2^-$, (CH$_2$)$_m$OPO$_3^{-2}$, and NHC(O)(CH$_2$)$_m$CO$_2^-$, and esters and salts thereof, wherein each R$_g$ is independently H or (C$_1$-C$_8$)alkyl, and the subscript m is an integer of from 0 to 6;

$R_h$ and $R_w$ are H or a group having from 1 to 30 atoms selected from C, N, O, P, and S and which is cyclic, acyclic, or a combination thereof.

15. A method of inhibiting miRNA activity in Nitro or in viNo comprising introducing the inhibitor composition of claim 1 to a location in vitro or in vivo where miRNA activity exists.

16. A method of treating a condition characterized by overexpression of miRNA comprising administering the inhibitor composition of claim 1 to a subject at a concentration sufficient to inhibit the action of said miRNA.

* * * * *

```
SEQUENCE LISTING

<160> NUMBER OF SEQ ID NOS: 20

<210> SEQ ID NO 1
<211> LENGTH: 22
<212> TYPE: RNA
<213> ORGANISM: Artificial Sequence
<220> FEATURE:
<223> OTHER INFORMATION: RNA mature strand Let7c inhibitor

<400> SEQUENCE: 1
ugagguagua gguuguaugg uu                                                22

<210> SEQ ID NO 2
<211> LENGTH: 22
<212> TYPE: DNA
<213> ORGANISM: Artificial Sequence
<220> FEATURE:
<223> OTHER INFORMATION: DNA equivalent mature strand Let7cT

<400> SEQUENCE: 2
tgaggtagta ggttgtatgg tt                                                22

<210> SEQ ID NO 3
<211> LENGTH: 22
<212> TYPE: DNA
<213> ORGANISM: Artificial Sequence
<220> FEATURE:
<223> OTHER INFORMATION: DNA complement Let7cTcomp

<400> SEQUENCE: 3
aaccatacaa cctactacct ca                                                22

<210> SEQ ID NO 4
<211> LENGTH: 22
<212> TYPE: DNA
<213> ORGANISM: Artificial Sequence
<220> FEATURE:
<223> OTHER INFORMATION: RNA Let7cTcomp with 2'-OMe
<220> FEATURE:
<221> NAME/KEY: modified_base
<222> LOCATION: (1)..(22)
<223> OTHER INFORMATION: All bases contain 2'-OMe

<400> SEQUENCE: 4
```
aaccatacaa cctactacct ca                                                    22

<210> SEQ ID NO 5
<211> LENGTH: 22
<212> TYPE: DNA
<213> ORGANISM: Artificial Sequence
<220> FEATURE:
<223> OTHER INFORMATION: Let7cTcomp with 3' MGB
<220> FEATURE:
<221> NAME/KEY: modified_base
<222> LOCATION: (22)..(22)
<223> OTHER INFORMATION: n is a conjugated to minor groove binder (MGB)
<220> FEATURE:
<221> NAME/KEY: misc_feature
<222> LOCATION: (22)..(22)
<223> OTHER INFORMATION: n is a, c, g, or t

<400> SEQUENCE: 5
aaccatacaa cctactacct cn                                                    22

<210> SEQ ID NO 6
<211> LENGTH: 22
<212> TYPE: DNA
<213> ORGANISM: Artificial Sequence
<220> FEATURE:
<223> OTHER INFORMATION: Let7cTcomp with Super A bases
<220> FEATURE:
<221> NAME/KEY: modified_base
<222> LOCATION: (2)..(2)
<223> OTHER INFORMATION: n is Super A base
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: modified_base
<222> LOCATION: (5)..(5)
<223> OTHER INFORMATION: n is Super A base
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (7)..(7)
<223> OTHER INFORMATION: n is Super A base
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: modified_base
<222> LOCATION: (10)..(10)
<223> OTHER INFORMATION: n is Super A base
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: modified_base
<222> LOCATION: (14)..(14)
<223> OTHER INFORMATION: n is Super A base
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: modified_base
<222> LOCATION: (17)..(17)
<223> OTHER INFORMATION: n is Super A base
<220> FEATURE:
<221> NAME/KEY: misc_feature
<222> LOCATION: (17)..(17)
<223> OTHER INFORMATION: n is a, c, g, or t

<400> SEQUENCE: 6
anccntncan cctnctncct ca                                             22

<210> SEQ ID NO 7
<211> LENGTH: 22
<212> TYPE: DNA
<213> ORGANISM: Artificial Sequence
<220> FEATURE:
<223> OTHER INFORMATION: Let7cTcomp with 5' MGB
<220> FEATURE:
<221> NAME/KEY: modified_base
<222> LOCATION: (1)..(1)
<223> OTHER INFORMATION: n is a conjugated to minor groove binder (MGB)
<220> FEATURE:
<221> NAME/KEY: misc_feature
<222> LOCATION: (1)..(1)
<223> OTHER INFORMATION: n is a, c, g, or t

<400> SEQUENCE: 7
naccatacaa cctactacct ca                                             22

<210> SEQ ID NO 8
<211> LENGTH: 22
<212> TYPE: DNA
<213> ORGANISM: Artificial Sequence
<220> FEATURE:
<223> OTHER INFORMATION: Let7cTcomp with 2'-OMe RNA and Super A bases
<220> FEATURE:
<221> NAME/KEY: modified_base
<222> LOCATION: (1)..(1)
<223> OTHER INFORMATION: Contains 2'-OMe
<220> FEATURE:
<221> NAME/KEY: modified_base
<222> LOCATION: (2)..(2)
<223> OTHER INFORMATION: n is Super A base
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: modified_base
<222> LOCATION: (3)..(4)
<223> OTHER INFORMATION: Contains 2'-OMe
<220> FEATURE:
<221> NAME/KEY: modified_base
<222> LOCATION: (5)..(5)
<223> OTHER INFORMATION: n is Super A base
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (6)..(6)
<223> OTHER INFORMATION: Contains 2'-OMe
<220> FEATURE:
<221> NAME/KEY: modified_base
<222> LOCATION: (7)..(7)
<223> OTHER INFORMATION: n is Super A base
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: modified_base
<222> LOCATION: (8)..(9)
<223> OTHER INFORMATION: Contains 2'-OMe
<220> FEATURE:
<221> NAME/KEY: modified_base
<222> LOCATION: (10)..(10)
<223> OTHER INFORMATION: n is Super A base
<220> FEATURE:
<221> NAME/KEY: misc_feature
<222> LOCATION: (10)..(10)
<223> OTHER INFORMATION: n is a, c, g, or t
<220> FEATURE:

```
<221> NAME/KEY: modified_base
<222> LOCATION: (11)..(13)
<223> OTHER INFORMATION: Contains 2'-OMe
<220> FEATURE:
<221> NAME/KEY: modified_base
<222> LOCATION: (14)..(14)
<223> OTHER INFORMATION: n is Super A base
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: modified_base
<222> LOCATION: (15)..(16)
<223> OTHER INFORMATION: Contains 2'-OMe
<220> FEATURE:
<221> NAME/KEY: modified_base
<222> LOCATION: (17)..(17)
<223> OTHER INFORMATION: n is Super A base
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: modified_base
<222> LOCATION: (18)..(22)
<223> OTHER INFORMATION: Contains 2'-OMe

<400> SEQUENCE: 8
anccntncan cctnctncct ca                                            22

<210> SEQ ID NO 9
<211> LENGTH: 22
<212> TYPE: DNA
<213> ORGANISM: Artificial Sequence
<220> FEATURE:
<223> OTHER INFORMATION: Let7cTcomp with 5' MGB and 2'-OMe RNA
<220> FEATURE:
<221> NAME/KEY: modified_base
<222> LOCATION: (1)..(1)
<223> OTHER INFORMATION: n is a conjugated to minor groove binder (MGB)
<220> FEATURE:
<221> NAME/KEY: modified_base
<222> LOCATION: (1)..(22)
<223> OTHER INFORMATION: All bases contain 2'-OMe
<220> FEATURE:
<221> NAME/KEY: misc_feature
<222> LOCATION: (1)..(1)
<223> OTHER INFORMATION: n is a, c, g, or t

<400> SEQUENCE: 9
naccatacaa cctactacct ca                                            22

<210> SEQ ID NO 10
<211> LENGTH: 22
<212> TYPE: DNA
<213> ORGANISM: Artificial Sequence
<220> FEATURE:
<223> OTHER INFORMATION: Let7cTcomp with 3' MGB and 2'-OMe
<220> FEATURE:
<221> NAME/KEY: modified_base
<222> LOCATION: (1)..(22)
<223> OTHER INFORMATION: All bases contain 2'-OMe
<220> FEATURE:
<221> NAME/KEY: modified_base
<222> LOCATION: (22)..(22)
<223> OTHER INFORMATION: n is a conjugated to minor groove binder (MGB)
<220> FEATURE:
<221> NAME/KEY: misc_feature
<222> LOCATION: (22)..(22)
<223> OTHER INFORMATION: n is a, c, g, or t

<400> SEQUENCE: 10
aaccatacaa cctactacct cn                                            22
```

<210> SEQ ID NO 11
<211> LENGTH: 22
<212> TYPE: RNA
<213> ORGANISM: Artificial Sequence
<220> FEATURE:
<223> OTHER INFORMATION: RNA mature strand Mir21

<400> SEQUENCE: 11
uagcuuauca gacugauguu ga                                              22

<210> SEQ ID NO 12
<211> LENGTH: 22
<212> TYPE: DNA
<213> ORGANISM: Artificial Sequence
<220> FEATURE:
<223> OTHER INFORMATION: DNA equivalent mature strand Mir21T

<400> SEQUENCE: 12
tagcttatca gactgatgtt ga                                              22

<210> SEQ ID NO 13
<211> LENGTH: 22
<212> TYPE: DNA
<213> ORGANISM: Artificial Sequence
<220> FEATURE:
<223> OTHER INFORMATION: DNA complement Mir21Tcomp

<400> SEQUENCE: 13
tcaacatcag tctgataagc ta                                              22

<210> SEQ ID NO 14
<211> LENGTH: 22
<212> TYPE: DNA
<213> ORGANISM: Artificial Sequence
<220> FEATURE:
<223> OTHER INFORMATION: Mir21Tcomp with 2'-OMe
<220> FEATURE:
<221> NAME/KEY: modified_base
<222> LOCATION: (1)..(22)
<223> OTHER INFORMATION: All bases contain 2'-OMe

<400> SEQUENCE: 14
tcaacatcag tctgataagc ta                                              22

<210> SEQ ID NO 15
<211> LENGTH: 22
<212> TYPE: DNA
<213> ORGANISM: Artificial Sequence
<220> FEATURE:
<223> OTHER INFORMATION: Mir21Tcomp with 3' MGB
<220> FEATURE:
<221> NAME/KEY: modified_base
<222> LOCATION: (22)..(22)
<223> OTHER INFORMATION: n is a conjugated to minor groove binder (MGB)
<220> FEATURE:
<221> NAME/KEY: misc_feature
<222> LOCATION: (22)..(22)
<223> OTHER INFORMATION: n is a, c, g, or t

<400> SEQUENCE: 15
tcaacatcag tctgataagc tn                                              22

<210> SEQ ID NO 16
<211> LENGTH: 22
<212> TYPE: DNA
<213> ORGANISM: Artificial Sequence
<220> FEATURE:

```
<223> OTHER INFORMATION: Mir21Tcomp with Super A bases
<220> FEATURE:
<221> NAME/KEY: modified_base
<222> LOCATION: (3)..(4)
<223> OTHER INFORMATION: n is Super A base
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (6)..(6)
<223> OTHER INFORMATION: n is Super A base
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (9)..(9)
<223> OTHER INFORMATION: n is Super A base
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (15)..(15)
<223> OTHER INFORMATION: n is Super A base
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (18)..(18)
<223> OTHER INFORMATION: n is Super A base
<220> FEATURE:
<221> NAME/KEY: misc_feature
<222> LOCATION: (18)..(18)
<223> OTHER INFORMATION: n is a, c, g, or t

<400> SEQUENCE: 16
tcnncntcng tctgntangc ta                                              22

<210> SEQ ID NO 17
<211> LENGTH: 22
<212> TYPE: DNA
<213> ORGANISM: Artificial Sequence
<220> FEATURE:
<223> OTHER INFORMATION: Mir21Tcomp with 5' MGB
<220> FEATURE:
<221> NAME/KEY: modified_base
<222> LOCATION: (1)..(1)
<223> OTHER INFORMATION: n is t conjugated to minor groove binder (MGB0
<220> FEATURE:
<221> NAME/KEY: misc_feature
<222> LOCATION: (1)..(1)
<223> OTHER INFORMATION: n is a, c, g, or t

<400> SEQUENCE: 17
ncaacatcag tctgataagc ta                                              22

<210> SEQ ID NO 18
<211> LENGTH: 22
<212> TYPE: DNA
<213> ORGANISM: Artificial Sequence
<220> FEATURE:
<223> OTHER INFORMATION: Mir21Tcomp with 2'-OMe and Super A bases
<220> FEATURE:
<221> NAME/KEY: modified_base
<222> LOCATION: (1)..(2)
<223> OTHER INFORMATION: Contains 2'-OMe
<220> FEATURE:
<221> NAME/KEY: modified_base
```

-continued

```
<222> LOCATION: (3)..(4)
<223> OTHER INFORMATION: n is Super A base
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: modified_base
<222> LOCATION: (5)..(5)
<223> OTHER INFORMATION: Contains 2'-OMe
<220> FEATURE:
<221> NAME/KEY: modified_base
<222> LOCATION: (6)..(6)
<223> OTHER INFORMATION: n is Super A base
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (7)..(8)
<223> OTHER INFORMATION: Contains 2'-OMe
<220> FEATURE:
<221> NAME/KEY: modified_base
<222> LOCATION: (9)..(9)
<223> OTHER INFORMATION: n is Super A base
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: modified_base
<222> LOCATION: (10)..(14)
<223> OTHER INFORMATION: Contains 2'-OMe
<220> FEATURE:
<221> NAME/KEY: modified_base
<222> LOCATION: (15)..(15)
<223> OTHER INFORMATION: n is Super A base
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (16)..(17)
<223> OTHER INFORMATION: Contains 2'-OMe
<220> FEATURE:
<221> NAME/KEY: modified_base
<222> LOCATION: (18)..(18)
<223> OTHER INFORMATION: n is Super A base
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: modified_base
<222> LOCATION: (19)..(21)
<223> OTHER INFORMATION: Contains 2'-OMe

<400> SEQUENCE: 18
tcnncntcng tctgntangc ta                                              22

<210> SEQ ID NO 19
<211> LENGTH: 22
<212> TYPE: DNA
<213> ORGANISM: Artificial Sequence
<220> FEATURE:
<223> OTHER INFORMATION: Mir21Tcomp with 5' MGB and 2'-OMe
<220> FEATURE:
<221> NAME/KEY: modified_base
<222> LOCATION: (1)..(1)
<223> OTHER INFORMATION: n is t conjugated to minor groove binder (MGB)
<220> FEATURE:
<221> NAME/KEY: modified_base
<222> LOCATION: (1)..(22)
<223> OTHER INFORMATION: All bases contain 2'-OMe
<220> FEATURE:
```

```
-continued

<221> NAME/KEY: misc_feature
<222> LOCATION: (1)..(1)
<223> OTHER INFORMATION: n is a, c, g, or t

<400> SEQUENCE: 19
ncaacatcag tctgataagc ta                                            22

<210> SEQ ID NO 20
<211> LENGTH: 22
<212> TYPE: DNA
<213> ORGANISM: Artificial Sequence
<220> FEATURE:
<223> OTHER INFORMATION: Mir2Tcomp with 3' MGB and 2'-OMe
<220> FEATURE:
<221> NAME/KEY: modified_base
<222> LOCATION: (1)..(22)
<223> OTHER INFORMATION: All bases contain 2'-OMe
<220> FEATURE:
<221> NAME/KEY: modified_base
<222> LOCATION: (22)..(22)
<223> OTHER INFORMATION: n is a conjugated to minor groove binder (MGB)
<220> FEATURE:
<221> NAME/KEY: misc_feature
<222> LOCATION: (22)..(22)
<223> OTHER INFORMATION: n is a, c, g, or t

<400> SEQUENCE: 20
tcaacatcag tctgataagc tn                                            22
```